United States Patent
Towson

(10) Patent No.: US 7,786,329 B2
(45) Date of Patent: *Aug. 31, 2010

(54) PROCESS FOR PREPARING ESTER OXAZOLIDINE COMPOUNDS AND THEIR CONVERSION TO FLORFENICOL

(75) Inventor: James C. Towson, Flemington, NJ (US)

(73) Assignee: Intervet Inc., Summit, NJ (US)

( * ) Notice: Subject to any disclaimer, the term of this patent is extended or adjusted under 35 U.S.C. 154(b) by 864 days.

This patent is subject to a terminal disclaimer.

(21) Appl. No.: 11/515,135

(22) Filed: Aug. 31, 2006

(65) Prior Publication Data

US 2007/0055080 A1 Mar. 8, 2007

Related U.S. Application Data

(60) Provisional application No. 60/714,685, filed on Sep. 7, 2005.

(51) Int. Cl.
*C07C 233/05* (2006.01)

(52) U.S. Cl. ...................... 564/212; 564/211
(58) Field of Classification Search ................. 564/211, 564/212
See application file for complete search history.

(56) References Cited

U.S. PATENT DOCUMENTS 7,126,005 B2 * 10/2006 Handa et al. ................. 548/215
2005/0075506 A1   4/2005 Handa et al.

FOREIGN PATENT DOCUMENTS

WO   WO 03/077828   9/2003

OTHER PUBLICATIONS

Badr et al, Bull. Chem. Soc. Japan, vol. 54, 1844-1847, 1981.*
International Serach Report, International Application PCT/US2006/034370, Date of Mailing: Feb. 21, 2007.

* cited by examiner

*Primary Examiner*—Shailendra Kumar

(57) ABSTRACT

A process for preparing ester oxazolidine compounds is disclosed. These compounds are useful intermediates in processes for making Florfenicol.

85 Claims, No Drawings

PROCESS FOR PREPARING ESTER OXAZOLIDINE COMPOUNDS AND THEIR CONVERSION TO FLORFENICOL

CROSS REFERENCE TO RELATED APPLICATIONS

This application is a non-provisional application that claims priority under 35 U.S.C. §119(e) of provisional application U.S. Ser. No. 60/714,685 filed Sep. 7, 2005, the contents of which are hereby incorporated by reference in their entireties.

TECHNICAL FIELD

The present invention relates generally to a new process for preparing oxazolidine protected aminodiol compounds. These compounds are useful intermediates in the process for making Florfenicol.

BACKGROUND OF THE INVENTION

Florfenicol is a broad spectrum antibiotic of Formula I

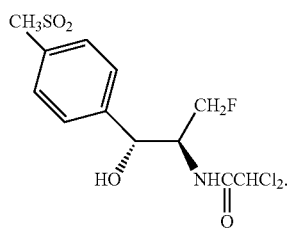

Formula I

It has wide spread application in veterinary medicine for the treatment of both Gram positive and Gram negative bacteria as well as rickettsial infections. Florfenicol is also known as [R-(R*,S*)]-2,2-Dichloro-N-[1-(fluoromethyl)-2-hydroxy-2-[4-(methylsulfonyl)phenyl]ethyl]acetamide.

Commonly-assigned U.S. Pat. No. 5,663,361, the disclosure of which is incorporated herein by reference, describes the synthesis of Florfenicol intermediates and their use in processes for making Florfenicol. The primary advantage discussed therein is that the process eliminated the prior art's requirement to isolate the aminodiol sulfone (ADS) from the reaction vessel before proceeding with the Florfenicol synthesis.

More recently, U.S. Patent 2005/0075506 A1 described a process for preparing a compound of Formula II that is useful as an intermediate in the synthesis of Florfenicol.

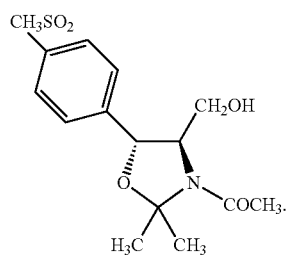

Formula II

The process called for reacting the hydrochloride salt of an optically pure aminodiol compound of Formula III with acetone followed by acetyl chloride to give a compound of Formula II. The compound of Formula II is then reacted further to give Florfenicol of Formula I.

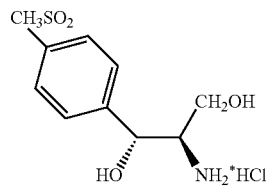

Formula III

A major drawback of the process disclosed in 2005/0075506 A1 is the use of the aminodiol starting material of Formula III. The aminodiol compound of Formula III is expensive. It is also difficult to isolate and handle due to its amphoteric nature.

The present invention addresses this shortcoming and provides a still further alternative method of preparing useful intermediates included in the synthesis of Florfenicol.

SUMMARY OF THE INVENTION

In one embodiment, the present invention includes a process for preparing an oxazolidine protected aminodiol compound of Formula V:

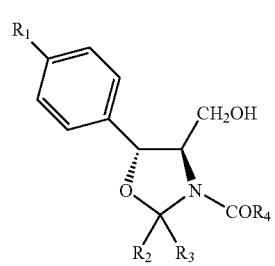

Formula V wherein:

$R_1$ is hydrogen, methylthio, methylsulfoxy, methylsulfonyl, fluoromethylthio, fluoromethylsulfoxy, fluoromethylsulfonyl, nitro, fluoro, bromo, chloro, acetyl, benzyl, phenyl, halo substituted phenyl, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{2-6}$ heterocyclic group;

$R_2$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl, or $C_{2-6}$ heterocyclic group;

$R_3$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl or $C_{2-6}$ heterocyclic group; and $R_4$ is hydrogen, OH, $C_{1-6}$ alkyl, $C_{1-6}$ haloalkyl, $C_{3-8}$ cycloalkyl, benzyl, phenyl or $C_{1-6}$ phenylalkyl group, where the phenyl ring may be substituted by one or two halogens, $C_{1-6}$ alkyl, or $C_{1-6}$ alkoxy.

In another preferred embodiment, the present invention includes a process for preparing an oxazolidine protected aminodiol compound of Formula XII:

Formula XII

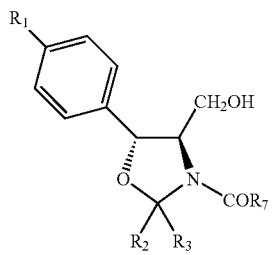

wherein:

$R_1$, $R_2$ and $R_3$ are as defined above; and $R_7$ is hydrogen, $C_{1-6}$ alkyl, $C_{1-6}$ haloalkyl, $C_{1-6}$ dihaloalkyl, $C_{1-6}$ trihaloalkyl, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{2-6}$ heterocyclic, benzyl, phenyl or phenyl alkyl where the phenyl ring may be substituted by one or two halogens, $C_{1-6}$ alkyl or $C_{1-6}$ alkoxy. Preferably, $R_7$ is $CH_2Cl$, $CHCl_2$, $CCl_3$, $CH_2Br$, $CHBr_2$, $CBr_3$, $CH_2F$, $CHF_2$, or $CF_3$.

In one embodiment, the process includes the steps of:

a) reacting a compound of Formula VI:

Formula VI

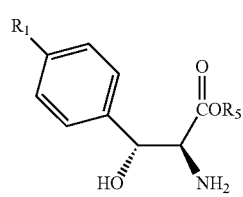

wherein:

$R_1$ is as defined above and $R_5$ is hydrogen, $C_{1-6}$ alkyl, $C_{3-8}$ cycloalkyl, benzyl, phenyl or $C_{1-6}$ phenylalkyl, in a vessel with a reducing agent in an alcoholic solvent to form an aminodiol compound of Formula VII:

Formula VII

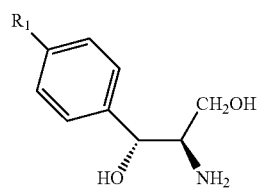

wherein $R_1$ is as defined above;

b) reacting the aminodiol compound of Formula VII in the vessel without isolation (i.e., in situ) with an oxazolidine forming reagent to form a compound of Formula VIII:

Formula VIII

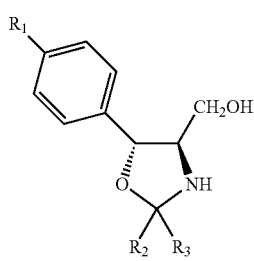

wherein $R_1$, $R_2$ and $R_3$ are as defined above; and c) reacting the compound of Formula VIII in the vessel without isolation (i.e., in situ) with a first N-acylating agent to form an oxazolidine protected aminodiol compound of Formula V.

In another preferred embodiment, the process includes the steps of:

a) reacting a compound of Formula VI in a vessel with an oxazolidine forming reagent to form the compound of Formula XIV:

Formula XIV

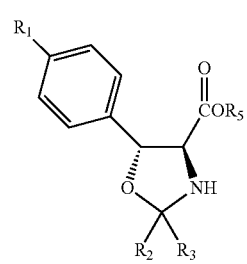

wherein $R_1$, $R_2$, $R_3$ and $R_5$ are as defined above;

b) reacting the compound of Formula XIV in the vessel without isolation (i.e., in situ) with a reducing agent in an alcoholic solvent to form the compound of Formula VIII;

c) reacting the compound of Formula VIII in the vessel without isolation (i.e., in situ) with a third N-acylating agent to form an oxazolidine protected aminodiol compound of Formula XII:

Formula XII

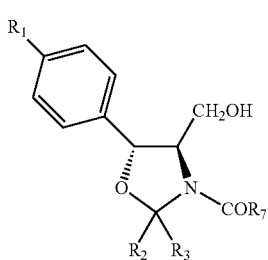

wherein $R_1$, $R_2$, $R_3$ and $R_7$ are as defined above;

d) fluorinating the compound of Formula XII with a fluorinating agent in the presence of an organic solvent to obtain the compound of Formula XIII:

Formula XIII

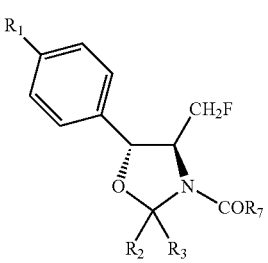

wherein $R_1$, $R_2$, $R_3$ and $R_7$ are as defined above;

e) selectively hydrolyzing the compound of Formula XIII with an acid or base catalyst to form the compound of Formula XI:

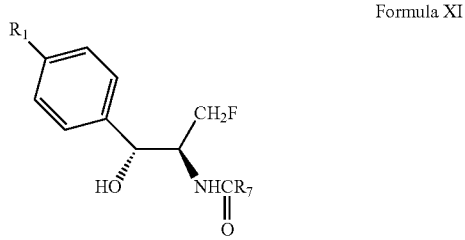

Formula XI wherein $R_1$ and $R_7$ are as defined above; and f) if necessary, purifying the compound of Formula XI with a mixture of a $C_{1-10}$ alkyl mono, di or tri alcohol and water to form the pure compound of Formula XI.

Applicants have now surprisingly found significant processing advantages for forming the oxazolidine protected aminodiol compounds of Formula V and Formula XII. The compounds of Formula V, or specifically Formula II, are obtained when an ester precursor to the aminodiol free base compound of Formula III are used as starting materials. Such esters generally correspond to Formula VI, and the ester of Formula IV is one particularly preferred ester:

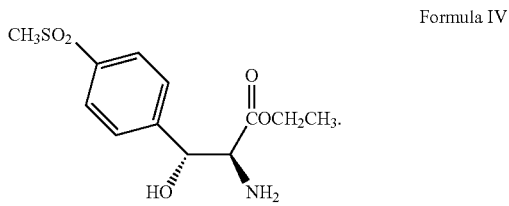

Formula IV

The use of the esters of Formulas IV and VI generates the expensive free base starting material of Formula III in situ, thereby eliminating the need to isolate this difficult to isolate compound. Yield losses for the free base starting material of Formula III due to isolation are thus eliminated with resulting increased yield and lower cost for the oxazolidine protected aminodiol compound of Formula V, or specifically the compound of Formula II.

Applicants have also surprisingly found a more efficient process for making the compound of Formula XII by generating the compound of Formula XIV. After preparation of the compound of Formula XIV the compound can then be converted without isolation (i.e., in situ) and in the same reaction vessel to the compound of Formula XII by reduction and acylation. The compound of Formula XII can then be converted to a compound of Formula XI, Florfenicol being the most preferred compound.

The present invention thus has the advantage of being an efficient and economical process for preparing Florfenicol, its analogs and oxazolidine intermediates related thereto.

DETAILED DESCRIPTION OF THE EMBODIMENTS

When utilized in the present specification and in the appended claims, the terms listed herein below, unless otherwise indicated, are defined as follows:

The term "alcoholic solvent" includes $C_1$ to $C_{10}$ alcohols such as methanol and ethanol and mixtures thereof, $C_2$ to $C_{10}$ dialcohols such as ethylene glycol and $C_1$ to $C_{10}$ trialcohols such as glycerin. Alternatively, the alcoholic solvent can be admixed with any suitable cosolvent. Such cosolvents can include other solvents which are miscible with the alcoholic solvent such as $C_4$ to $C_{10}$ alkanes, aromatic solvents such as benzene, toluene, xylenes, halobenzenes such as chlorobenzene, and ethers such as diethylether, tert-butylmethylether, isopropylether and tetrahydrofuran, or mixtures of any of the above solvents or cosolvents.

The term "alkyl" means a straight or branched alkyl such as methyl, ethyl, propyl, or sec-butyl. Alternatively, the number of carbons in alkyl may be specified. For example, "$C_1$ to $C_6$ alkyl" means an "alkyl" as described above containing 1 to 6 carbon atoms. "Haloalkyl" means an "alkyl" as described above wherein one or more hydrogens are replaced by halo.

The term "aryl" means phenyl, or phenyl substituted by $C_1$ to $C_6$ alkyl or halo.

"Substituted benzyl" means benzyl substituted by $C_1$ to $C_6$ alkyl or halo.

The term "halo" means fluoro, chloro, bromo or iodo.

The term "halo aryl" means phenyl substituted by halo.

In one aspect of the invention, there is provided a process for preparing an oxazolidine protected aminodiol compound of Formula V:

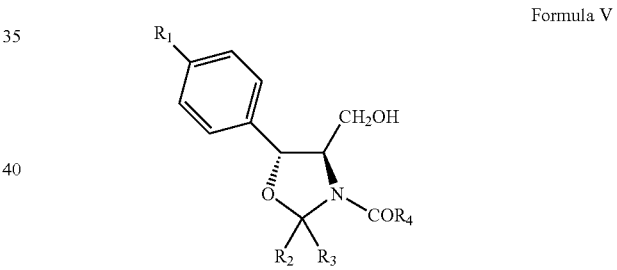

Formula V wherein:

$R_1$ is hydrogen, methylthio, methylsulfoxy, methylsulfonyl, fluoromethylthio, fluoromethylsulfoxy, fluoromethylsulfonyl, nitro, fluoro, bromo, chloro, acetyl, benzyl, phenyl, halo substituted phenyl, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{2-6}$ heterocyclic group;

$R_2$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl, or $C_{2-6}$ heterocyclic group;

$R_3$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl or $C_{2-6}$ heterocyclic group; and $R_4$ is hydrogen, OH, $C_{1-6}$ alkyl, $C_{1-6}$ haloalkyl, $C_{3-8}$ cycloalkyl, benzyl, phenyl or $C_{1-6}$ phenylalkyl group, where the phenyl ring may be substituted by one or two halogens, $C_{1-6}$ alkyl or $C_{1-6}$ alkoxy.

The compounds corresponding thereto are useful intermediates in the formation of Florfenicol and related compounds.

One preferred process corresponding to the invention includes the steps of:

a) reacting a compound of Formula VI:

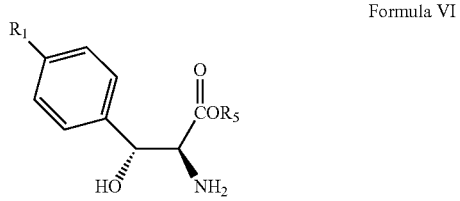

Formula VI wherein:

$R_1$ is as defined above and $R_5$ is hydrogen, $C_{1-6}$ alkyl, $C_{3-8}$ cycloalkyl, benzyl, phenyl or $C_{1-6}$ phenylalkyl, in a vessel with a reducing agent in an alcoholic solvent to form an aminodiol compound of Formula VII:

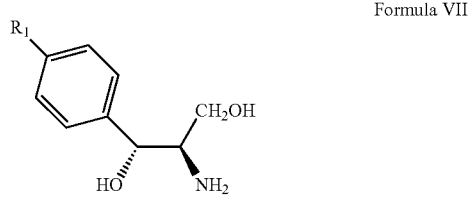

Formula VII wherein $R_1$ is as defined above;

b) reacting the aminodiol compound of Formula VII in the vessel without isolation (i.e., in situ) with an oxazolidine forming reagent to form a compound of Formula VIII:

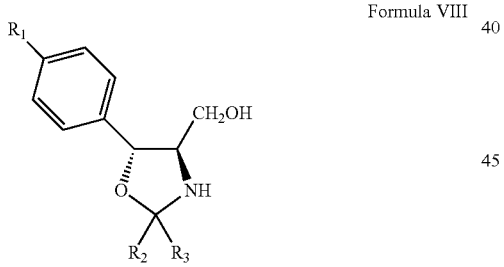

Formula VIII wherein $R_1$, $R_2$ and $R_3$ are as defined above; and c) reacting the compound of Formula VIII in the vessel without isolation (i.e., in situ) with a first N-acylating agent to form an oxazolidine protected aminodiol compound of Formula V.

Within the general process described above, there are certain currently preferred aspects of the invention:

$R_1$ is methylthio, methylsulfoxy, or methylsulfonyl. More preferably, $R_1$ is methylsulfonyl;

$R_2$ and $R_3$ are hydrogen, methyl, ethyl or propyl. More preferably, $R_2$ and $R_3$ are methyl;

$R_4$ is a methyl, ethyl, propyl or isopropyl group. More preferably, $R_4$ is methyl; and $R_5$ is methyl, ethyl, n-propyl, isopropyl, butyl, t-butyl, or pentyl. The compound of Formula IV is commercially available. Alternative compounds corresponding to Formula VI can be prepared using standard organic synthetic techniques without undue experimentation.

One preferred ester compound corresponding to Formula VI is

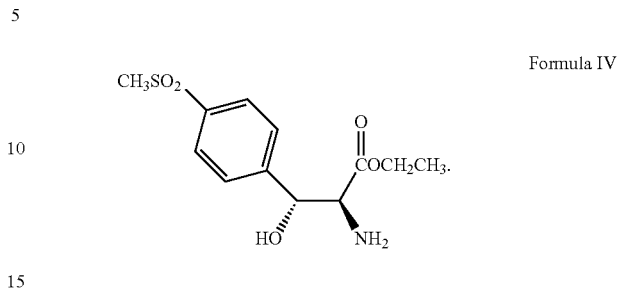

Formula IV

In another aspect of the invention, the ester compound of Formula VI is

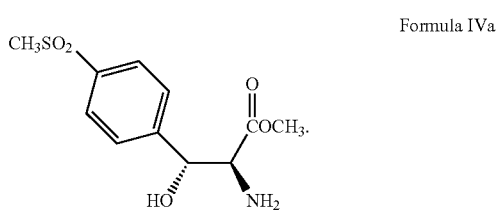

Formula IVa

In still further aspects, the esters correspond to

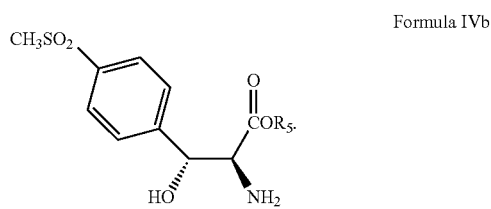

Formula IVb

In a more preferred embodiment when Florfenicol is the desired end product, the compound corresponding to Formula VI is the compound of Formula IV.

As mentioned above, the first part of the process calls for reacting a compound of Formula VI in a reaction vessel with a reducing agent. For purposes of the present invention, the term "reaction vessel" shall be understood to mean a container known to those of ordinary skill which is capable of holding the reactants and allowing the reaction step to proceed to completion. The size and type of vessel will, of course, depend upon the size of the batch and the specific reactants selected.

A wide range of suitable reducing agents can be employed in carrying out the process of the invention. A non-limiting list of suitable reducing agents include $NaBH_4$, $KBH_4$, $Ca(BH_4)_2$, and $LiBH_4$ and mixtures thereof when an alcoholic solvent is used. The alcoholic solvent can also be one of many art-recognized solvents but some preferred solvents include methanol, ethanol, propanol, isopropanol, butanol and pentanol and mixtures thereof. One preferred reducing agent is $KBH_4$.

The molar ratio of reducing agent, such as $KBH_4$, to the compound of Formula IV is between about 1:1 and about 2:1. Preferably, when the reducing agent is $KBH_4$, the molar ratio of $KBH_4$ to the compound of Formula IV is about 1.5:1 and the preferred solvent is methanol. This reduction can be carried out at a temperature of about 30° C. to about 80° C. in about 8 hours. Preferably, the temperature is below 60° C. and the time for the reaction to reach completion is under 6 hours.

In an alternative aspect of the invention, the artisan can use reducing agents such as $LiAlH_4$ or $NaAlH_4$ when anhydrous conditions are desired. In such situations, solvents like ether or tetrahydrofuran can be used.

Once the aminodiol compound corresponding to Formula VII has been made, it is reacted, preferably in the same vessel (i.e., in situ), with an oxazolidine forming reagent such as formaldehyde, acetone, 2-methoxypropene, 2,2-dimethoxypropane, 2,2-diethoxypropane and mixtures thereof, under conditions such as those set forth in the examples to make a compound of Formula VIII. One preferred aminodiol compound corresponding to Formula VII is

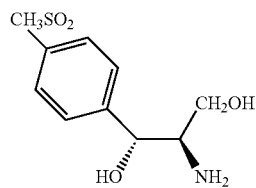

Formula VIIa

In a preferred embodiment when Florfenicol is the desired end product, the compound corresponding to Formula VIII is the compound:

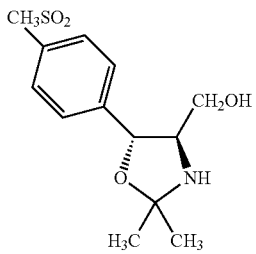

Formula VIIIa

In a preferred embodiment, the methanol solvent is removed by distillation and replaced with another solvent designated herein as an oxazolidine forming solvent such as toluene, xylene, hexane or a mixture thereof. The preferred oxazolidine forming solvent is toluene. The ratio of the oxazolidine forming solvent to methanol is about 0.5:1 to 3:1 with the preferred ratio of about 1:1. An oxazolidine forming reagent such as formaldehyde, acetone, 2-methoxypropene, 2,2-dimethoxypropane, 2,2-diethoxypropane and mixtures thereof is then added. One preferred oxazolidine forming reagent is acetone which is added in a ratio to toluene of about 0.5:1 to 3:1 with the preferred ratio of about 1:1. The reaction runs to completion to form the oxazolidine compound of Formula VIII over about 12-18 hours in the presence of a base designated herein as an oxazolidine promoting base such as potassium carbonate, sodium carbonate, trimethylamine or triethylamine. A preferred base is potassium carbonate or triethylamine. The oxazolidine forming reaction can be carried out at a temperature of about 65-85° C.

It is preferred that the compound of Formula VIII remain in the same vessel after completion of the reaction step when the first N-acylating agent is added. The nomenclature "first," "second" and "third" are used for describing the (1) N-acylating (first) agents so as to distinguish the agents used for making the oxazolidine protected aminodiol compounds of Formula V, from the (2) N-acylating agents (second) which are used in the formation of the compounds of Formula XI after the intermediate of Formula X has been formed, from the (3) N-acylating agents (third) used during the process to form the oxazolidine protected aminodiol compounds of Formula XII. Thus, some preferred first N-acylating compounds are of the formula $R_6COR_4$ wherein:

$R_4$ is hydrogen, OH, $C_{1-6}$ alkyl, $C_{1-6}$ haloalkyl, $C_{3-8}$ cycloalkyl, benzyl, phenyl or $C_{1-6}$ phenylalkyl group, where the phenyl ring may be substituted by one or two halogens, $C_{1-6}$ alkyl or $C_{1-6}$ alkoxy; and $R_6$ is halo, or $C_{1-6}$ alkoxy.

Some more preferred first acylating agents include acetyl chloride, acetyl bromide, propionyl chloride, propionyl bromide, butyl chloride, methyl chloroformate, ethyl chloroformate, propyl chloroformate and mixtures thereof.

In a preferred embodiment when Florfenicol is the desired end product, the compound corresponding to Formula V is the compound:

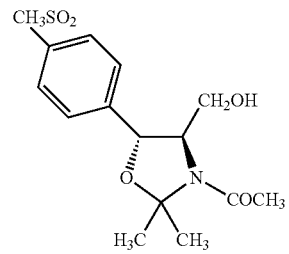

Formula Va

In a preferred embodiment, a base such as potassium carbonate, sodium carbonate, trimethylamine or triethylamine is added in a molar equivalent ratio to the compound of Formula VII of about 1:1 to 1:3. The preferred base is potassium carbonate or triethylamine and the preferred molar equivalent ratio is about 1.1 to 1. The preferred first N-acylating agent acetyl chloride is added in a molar ratio to the compound of Formula VII of about 1:1 to 3:1 with the preferred ratio being 1.1:1. Reaction temperature is about 20-30° C. and the reaction completes in about 2-4 hours.

After the oxazolidine protected aminodiol compound of Formula V has been prepared, it can be used in the synthesis of Florfenicol and related compounds. Thus, in a further aspect of the invention, the inventive process continues by fluorinating the compound of Formula V:

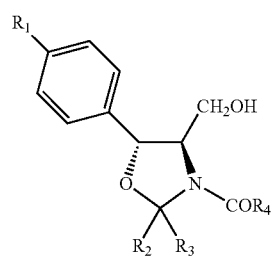

Formula V wherein $R_1$, $R_2$, $R_3$ and $R_4$ are as defined above, with a fluorinating agent in the presence of an organic solvent to obtain a compound of Formula IX:

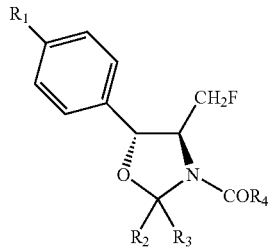

Formula IX wherein $R_1$, $R_2$, $R_3$ and $R_4$ are as defined above.

In one preferred aspect of this embodiment when Florfenicol is the desired end product, the compound corresponding to Formula IX is specifically:

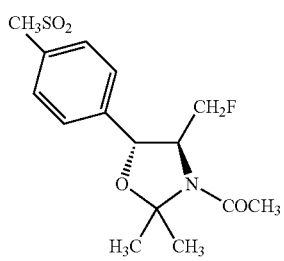

Formula IXa

Suitable fluorinating agents include, without limitation, N-(2-chloro-1,1,2-trifluoroethyl)diethylamine, N-(2-chloro-1,1,2-trifluoroethyl)dimethylamine, N-(2-chloro-1,1,2-trifluoroethyl)dipropylamine, N-(2-chloro-1,1,2-trifluoroethyl)pyrrolidine, N-(2-chloro-1,1,2-trifluoroethyl)-2-methylpyrrolidine, N-(2-chloro-1,1,2-trifluoroethyl)-4-methylpiperazine, N-(2-chloro-1,1,2-trifluoroethyl)-morpholine, N-(2-chloro-1,1,2-trifluoroethyl)piperidine, 1,1,2,2-tetrafluoroethyl-N,N-dimethylamine, (Diethylamino)sulfurtrifluoride, Bis-(2-methoxyethyl)aminosulfurtrifluoride, N,N-diethyl-1,1,2,3,3,3-hexafluoro-1-propanamine (Ishikawa Reagent) and mixtures thereof. One preferred fluorinating agent is N,N-diethyl-1,1,2,3,3,3-hexafluoro-1-propanamine.

The molar ratio of the fluorinating agent such as N,N-diethyl-1,1,2,3,3,3-hexafluoro-1-propanamine to the compound according to Formula V is between about 1:1 and about 2:1. Preferably, the molar ratio of the N,N-diethyl-1,1,2,3,3, 3-hexafluoro-1-propanamine to the compound of Formula V is about 1.5:1. The fluorinating step can be carried out at a temperature of from about 80° C. to about 110° C. and at a pressure of about 60 psi.

The organic solvent used during the fluorinating step is preferably 1,2-dichloroethane, methylene chloride, chloroform, chlorobenzene, chlorinated hydrocarbons or mixtures thereof. A more preferred organic solvent is methylene chloride.

After the compound of Formula IX has been made, it is hydrolyzed with acid to form the compound of Formula X:

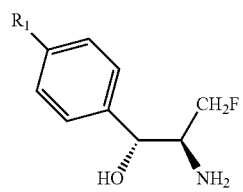

Formula X wherein $R_1$ is as defined above, preferably, $R_1$ is $CH_3SO_2$.

The acid used in this part of the process can be an inorganic acid like aqueous hydrochloric acid, sulfuric acid, or phosphoric acid or an organic acid like methanesulfonic acid. The hydrolyzing step is preferably carried out by heating the compound of Formula IX with 6N aqueous hydrochloric acid at a temperature of from about 90° C. to about 105° C. for about 60 minutes. Other suitable hydrolyzing steps will be apparent to those of ordinary skill.

In one preferred aspect of this embodiment when Florfenicol is the desired end product, the compound corresponding to Formula X is:

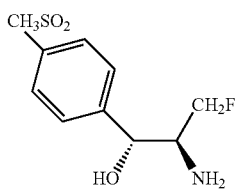

Formula Xa

After hydrolysis has been completed, the compound of Formula X is reacted without isolation (i.e., in situ) with a second N-acylating agent to make compounds of Formula XI:

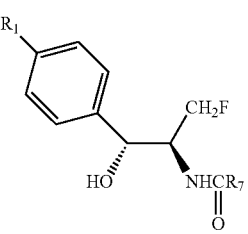

Formula XI wherein $R_1$ is the same as above, preferably $CH_3SO_2$; and $R_7$ is hydrogen, $C_{1-6}$ alkyl, $C_{1-6}$ haloalkyl, $C_{1-6}$ dihaloalkyl, $C_{1-6}$ trihaloalkyl, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{2-6}$ heterocyclic benzyl, phenyl or phenyl alkyl where the phenyl ring may be substituted by one or two halogens, $C_{1-6}$ alkyl or $C_{1-6}$ alkoxy. Preferably, $R_7$ is $CH_2Cl$, $CHCl_2$, $CCl_3$, $CH_2Br$, $CHBr_2$, $CBr_3$, $CH_2F$, $CHF_2$, or $CF_3$. Thus, one preferred compound of Formula XI is:

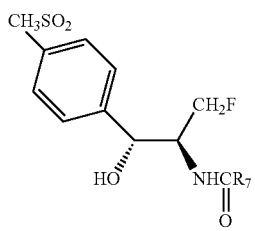

Formula XIa wherein $R_7$ is as defined above.

In one preferred aspect of this embodiment when Florfenicol is the desired end product, the compound corresponding to Formula XI is the compound of Formula I:

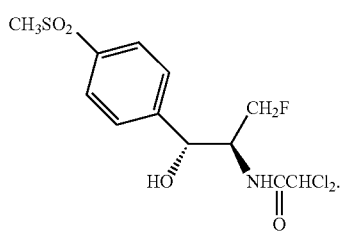

Formula I

Suitable second N-acylating compounds are of the formula $R_8COR_7$, wherein $R_7$ is the same as that described above and $R_8$ is OH, halo or $C_{1-6}$ alkoxy. Some more preferred second N-acylating agents include dichloroacetic acid or a reactive derivative thereof. A non-limiting list includes reagents such as methyldichloroacetate, ethyldichloroacetate, or dichloroacetylchloride.

The second N-acylation step is preferably carried out by reacting the compound of Formula X in methanol with methyldichloroacetate at a temperature of from about 20° C. to about 30° C. for about 12 hours.

After the compound of Formula XI is made and if necessary, the compound of Formula XI can optionally be purified by heating in a mixture of an alkyl mono, di or tri alcohols and water. The alcohols in this part of the process can be $C_{1-10}$ monoalcohols, $C_{1-10}$ dialcohols and $C_{1-10}$ trialcohols and mixtures thereof. A non-limiting list of the $C_{1-10}$ monoalcohols includes methanol, ethanol, propanol, isopropanol, butanol, sec-butanol, t-butanol and pentanol. One preferred $C_{1-10}$ monoalcohol is isopropanol. A non-limiting list of the $C_{1-10}$ dialcohols includes ethylene glycol, propylene glycol and butylene glycol of which propylene glycol is preferred. Glycerin is the preferred $C_{1-10}$ trialcohol. A $C_{1-10}$ monoalcohol is preferred for the purification. One most preferred $C_{1-10}$ monoalcohol is isopropanol.

The ratio of alcohol, such as isopropanol, to water is between 1:5 and 5:1. Preferably, when the alcohol is isopropanol, the ratio of isopropanol to water is 1:1. The compound of Formula XI is dissolved in a 1:1 mixture of isopropanol and water heated to the reflux point of the mixture. The solution is clarified by filtration with active carbon and a filter aid, then cooled to about 10-30° C. and the purified compound of Formula XI crystallizes from solution. Preferably, the solution is cooled to about 20-25° C. and the purified compound of Formula XI crystallizes from solution.

In a preferred embodiment when Florfenicol is the desired end product, the purified compound corresponding to Formula XI is the compound of Formula I.

In another preferred embodiment, the process corresponding to the invention includes the steps of:

a) reacting a compound of Formula VI in a vessel with an oxazolidine forming reagent to form the compound of Formula XIV:

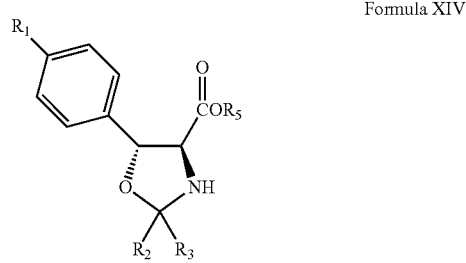

Formula XIV wherein $R_1$, $R_2$, $R_3$ and $R_5$ are as defined above;

b) reacting the compound of Formula XIV in the vessel without isolation (i.e., in situ) with a reducing agent in an alcoholic solvent to form a compound of Formula VIII:

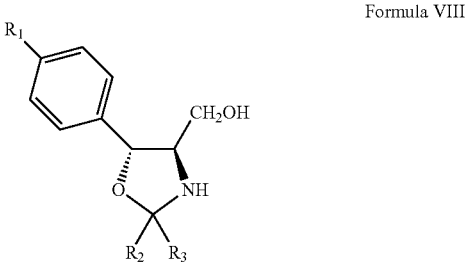

Formula VIII wherein $R_1$, $R_2$ and $R_3$ are as defined above;

c) reacting the compound of Formula VIII in the vessel without isolation (i.e., in situ) with a third N-acylating agent to form an oxazolidine protected aminodiol compound of Formula XII:

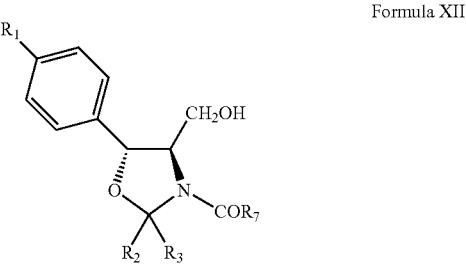

Formula XII wherein $R_1$, $R_2$, $R_3$ and $R_7$ are as defined above;

d) fluorinating the compound of Formula XII with a fluorinating agent in the presence of an organic solvent to obtain a compound of Formula XIII:

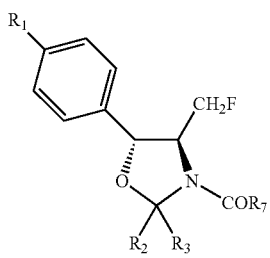

Formula XIII wherein $R_1$, $R_2$, $R_3$ and $R_7$ are as defined above;

e) selectively hydrolyzing the compound of Formula XIII with an acid or base catalyst to form the compound of Formula XI:

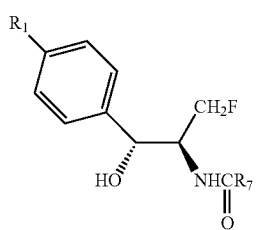

Formula XI wherein $R_1$ and $R_7$ are as defined above; and f) if necessary, purifying the compound of Formula XI with a mixture of a $Cl_{1-10}$ alkyl mono, di or tri alcohol and water to form the pure compound of Formula XI.

In the preferred embodiment described above, there are certain preferred aspects of the invention. One preferred aspect is that the compound of Formula VI reacts in a vessel with an oxazolidine forming reagent. A wide range of suitable oxazolidine forming reagents can be employed in carrying out the invention. A non-limiting list of suitable oxazolidine forming reagents include formaldehyde, acetone, 2-methoxypropene, 2,2-dimethoxypropane, 2,2-diethoxypropane and mixtures thereof. The solvent for the formation of compounds of Formula XIV can be the oxazolidine forming agent itself or a suitable organic solvent. Such solvents include but are not limited to alcoholic solvents such as methanol, ethanol, propanol, isopropanol, butanol, pentanol and mixtures thereof.

In a preferred embodiment, the oxazolidine forming reagent is added to the compound of Formula VI in an alcoholic solvent. The preferred oxazolidine forming reagent is 2,2-dimethoxypropane. 2,2-Dimethoxypropane is added to the compound of Formula VI in a ratio of between 1:1 and 5:1 with the preferred ratio of about 1:1. The preferred alcoholic solvent is methanol. The reaction runs to completion to form the ester oxazolidine compound of Formula XIV in the presence of a base designated herein as an ester oxazolidine promoting base such as lithium carbonate, lithium hydroxide triethylamine or trimethylamine. A preferred base is lithium carbonate. The ester oxazolidine forming reaction can be carried out at a temperature of less than 80° C.

In a preferred embodiment when Florfenicol is the desired end product, the compound corresponding to Formula XIV is the compound of Formula XIVa:

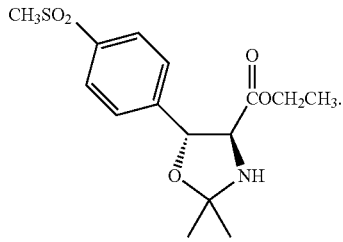

Formula XIVa

Preferably, the compound of Formula XIV remains in the same vessel after completion of the ester oxazolidine reaction when the reducing agent is added. A wide range of suitable reducing agents can be employed in carrying out the process of the invention to form the compound of Formula VIII. A non-limiting list of suitable reducing agents include $NaBH_4$, $KBH_4$, $Ca(BH_4)_2$, and $LiBH_4$ and mixtures thereof when an alcoholic solvent is used. The alcoholic solvent can also be one of many art-recognized solvents but some preferred solvents include methanol, ethanol, propanol, isopropanol, butanol and pentanol and mixtures thereof. One preferred reducing agent is $KBH_4$.

The molar ratio of reducing agent, such as $KBH_4$, to the compound of Formula VI is between about 1:1 and about 2:1. Preferably, when the reducing agent is $KBH_4$, the molar ratio of $KBH_4$ to the compound of Formula VI is about 1.5:1 and the preferred solvent is methanol. This reduction can be carried out at a temperature of about 30° C. to about 80° C. in about 8 hours. Preferably, the temperature is below 60° C. and the time for the reaction to reach completion is under 6 hours.

In an alternative aspect of the invention, the artisan can use reducing agents such as $LiAlH_4$ or $NaAlH_4$ when anhydrous conditions are desired. In such situations, solvents like ether or tetrahydrofuran can be used.

In a preferred embodiment when Florfenicol is the desired end product, the compound corresponding to Formula VIII is the compound of Formula VIIIa:

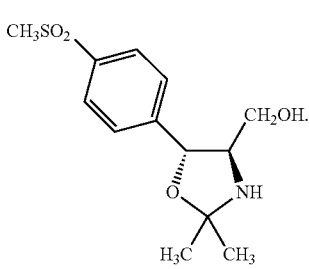

Formula VIIIa

It is preferred that after the compound of Formula VIII is made it is reacted preferably in the same vessel (i.e., in situ) with a suitable third N-acylating compound to form the compound of Formula XII. Some preferred third N-acylating compounds are of the formula $R_6COR_7$, wherein $R_6$ and $R_7$ are as defined above. In a preferred embodiment, $R_6$ is Cl and $R_7$ is $CH_2Cl$, $CHCl_2$, $CCl_3$, $CH_2Br$, $CHBr_2$, $CBr_3$, $CH_2F$, $CHF_2$, or $CF_3$.

Some preferred third N-acylating agents include alkylhaloacetic acid derivatives. A non-limiting list includes reagents such as methyldichloroacetate, ethyldichloroacetate, dichloroacetylchloride, methylchloroacetate, ethylchloroacetate, chloroacetylchloride, methyltrichloroacetate, ethyltrichloroacetate, trichloroacetylchloride, methyldifluoroacetate, ethyldifluoroacetate, difluoroacetylchloride, methylfluoroacetate, ethylfluoroacetate, fluoroacetylchloride, methyltrifluoroacetate, ethyltrifluoroacetate, trifluoroacetylchloride, dichloroacetylbromide, difluoroacetylbromide, acetylchloride and acetylbromide.

In a preferred embodiment when Florfenicol is the desired end product, the compound corresponding to Formula XII is the compound of Formula XIIa:

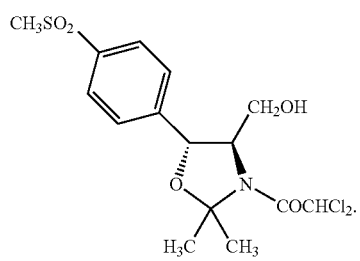

Formula XIIa

In a preferred embodiment, a base such as potassium carbonate, sodium carbonate, trimethylamine or triethylamine is added in a molar equivalent ratio to the compound of Formula VIIIa of about 1:1 to 1:3. The preferred base is potassium carbonate or triethylamine and the preferred molar equivalent ratio is about 1.1 to 1. The preferred N-acylating agent dichloroacetyl chloride is added in a molar ratio to the compound of Formula VIIIa of about 1:1 to 3:1 with the preferred ratio being 1.1:1. Reaction temperature is about 20-30° C. and the reaction completes in about 2-4 hours.

After the oxazolidine protected aminodiol compound of Formula XII has been prepared, it can be used in the synthesis of Florfenicol and related compounds. Thus, in a further aspect of the invention, the inventive process continues by fluorinating the compound of Formula XII:

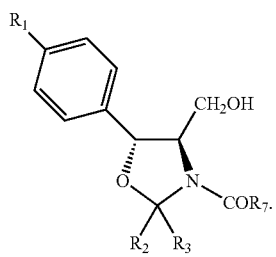

Formula XII wherein $R_1$, $R_2$, $R_3$ and $R_7$ are as defined above, with a fluorinating agent, as previously defined, in the presence of an organic solvent, as previously defined, to obtain a compound of Formula XIII:

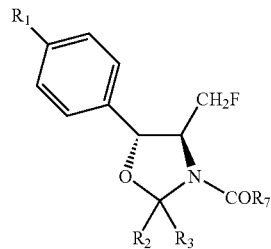

Formula XIII wherein $R_1$, $R_2$, $R_3$ and $R_7$ are as defined above.

In one preferred aspect of this embodiment when Florfenicol is the desired end product, the compound corresponding to Formula XIII is specifically the compound of Formula XIIIa:

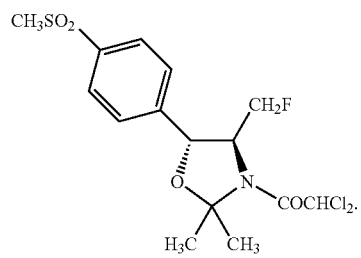

Formula XIIIa

After the compound of Formula XIII has been made, it is selectively hydrolyzed with acid or base catalyst to form the compound of Formula XI:

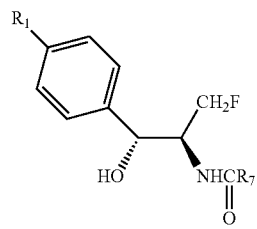

Formula XI wherein $R_1$ and $R_7$ are as defined above. Preferably, $R_1$ is methylsulfonyl and $R_7$ is $CH_2Cl$, $CHCl_2$, $CCl_3$, $CH_2Br$, $CHBr_2$, $CBr_3$, $CH_2F$, $CHF_2$, or $CF_3$.

A wide range of acid catalysts can be employed in carrying out the process of the invention. A non-limiting list of suitable acid catalysts include inorganic acids like dilute aqueous hydrochloric acid, sulfuric acid, or phosphoric acid or organic acids like methanesulfonic acid or p-toluene sulfonic acid. One preferred acid catalyst is p-toluene sulfonic acid. Similarly, a wide range of basic catalysts can be employed in carrying out the process of the invention. A non-limiting list of suitable basic catalysts include inorganic bases such as LiOH, NaOH, KOH, $Li_2CO_3$, $Na_2CO_3$, $K_2CO_3$ or organic bases such as sodium methoxide, sodium ethoxide, potassium methoxide and potassium ethoxide. One preferred basic catalyst is $K_2CO_3$. The selective hydrolyzing step is preferably carried out be heating the compound of Formula XII with p-toluene sulfonic acid in a mixture of an organic solvent and water at a temperature below 80° C. One preferred organic solvent is methylene chloride. Other suitable selective hydrolyzing steps will be apparent to those of ordinary skill.

In one preferred aspect of this embodiment when Florfenicol is the desired end product, the compound corresponding to Formula XI is the compound of Formula I.

After the compound of Formula XI is made and if necessary, it can optionally be purified by the process as described above. In a preferred embodiment when Florfenicol is the desired end product, the purified compound corresponding to Formula XI is the compound of Formula I.

EXAMPLES

The following preparative examples of preferred novel derivatives serve to provide further appreciation of the invention but are not meant in any way to restrict the effective scope of the invention.

Example 1

Preparation of (4R,5R)-3-acetyl-2,2-dimethyl-4-hydroxymethyl-5-[4-(methylsulfonyl)phenyl]-1,3-oxazolidine (Compound II)

(2S,3R)-Ethyl-2-amino-3-[4-(methylsulfonyl)phenyl]-3-hydroxy-propanoate (Compound IV) (100 g, 0.3480 moles) in 500 mL of methanol reacts with potassium borohydride (28.2 g, 0.5220 moles) over 4-8 hours at 50-60° C. to quantitatively yield (1R,2R)-2-amino-1-[4-(methylsulfonyl)phenyl]-1,3-propandiol (Compound VII: $R_1$ is methylsulfonyl) (85.36 g, 0.3480 moles) in solution. Toluene (500 mL) and acetone (500 mL) replace methanol which distills off. Addition of potassium carbonate (6.9 g, 0.0696 moles) with heating at 75-85° C. for 12-18 hours yields (4R,5R)-2,2-dimethyl-4-hydroxymethyl-5-[4-(methylsulfonyl)phenyl]-1,3-oxazolidine (Compound VIII: $R_1$ is methylsulfonyl and $R_2$ and $R_3$ are methyl). Addition of potassium carbonate (19.0 g, 0.1914 moles) and acetyl chloride (30.0 g, 0.3828 moles) at 20-25° C. for 2-4 hours then addition of water (500 mL) precipitates the crude product. Filtration, washing with water (250 mL) then drying yields (4R,5R)-3-acetyl-2,2-dimethyl-4-hydroxymethyl-5-[4-(methylsulfonyl)phenyl]-1,3-oxazolidine (Compound II).

Example 2

Preparation of (4R,5R)-3-acetyl-2,2-dimethyl-4-hydroxymethyl-5-[4-(methylsulfonyl)phenyl]-1,3-oxazolidine (Compound II)

(2S,3R)-Ethyl-2-amino-3-[4-(methylsulfonyl)phenyl]-3-hydroxy-propanoate (Compound IV) (100 g, 0.3480 moles) in methanol (450 mL) reacts with potassium borohydride (28.2 g, 0.5220 moles) over 4-8 hours at 50-60° C. to quantitatively yield (1R,2R)-2-amino-1-[4-(methylsulfonyl)phenyl]-1,3-propandiol (Compound VII: $R_1$ is methylsulfonyl) (85.4 g, 0.3480 moles) in solution. Toluene (450 mL) and acetone (450 mL) replace methanol which distills off. Addition of triethylamine (8.8 g, 0.0870 moles) with heating at 70-80° C. for 12-18 hours yields (4R,5R)-2,2-dimethyl-4-hydroxymethyl-5-[4-(methylsulfonyl)phenyl]-1,3-oxazolidine (Compound VIII: $R_1$ is methylsulfonyl and $R_2$ and $R_3$ are methyl). Addition of triethylamine (44.5 g, 0.4402 moles) and acetyl chloride (30.0 g, 0.3828 moles) at 20-25° C. for 2-4 hours then addition of water (500 mL) precipitates the crude product. Filtration, washing with water (200 mL) then drying yields (4R,5R)-3-acetyl-2,2-dimethyl-4-hydroxymethyl-5-[4-(methylsulfonyl)phenyl]-1,3-oxazolidine (Compound II).

Example 3

Preparation of (4R,5R)-3-acetyl-2,2-dimethyl-4-hydroxymethyl-5-[4-(methylsulfonyl)phenyl]-1,3-oxazolidine (Compound II)

(2S,3R)-Ethyl-2-amino-3-[4-(methylsulfonyl)phenyl]-3-hydroxy-propanoate (Compound IV) (100 g, 0.3480 moles) in tetrahydrofuran (500 mL) reacts with lithium aluminum hydride (16.0 g, 0.4224 moles) over 4-8 hours at 60-70° C. to quantitatively yield (1R,2R)-2-amino-1-[4-methylsulfonyl)phenyl]-1,3-propandiol (Compound VII: $R_1$ is methylsulfonyl) (85.36 g, 0.3480 moles). Addition of ethyl acetate (75 mL) destroys any excess lithium aluminum hydride. Addition of xylene (600 mL), 2-methoxypropene (37.6 g, 0.5220 moles), and p-toluenesulfonic acid monohydrate (6.6 g, 0.0348 moles) with agitation at 20-30° C. for 10-16 hours produces (4R,5R)-2,2-dimethyl-4-hydroxymethyl-5-[4-(methylsulfonyl)phenyl]-1,3-oxazolidine (Compound VIII: $R_1$ is methylsulfonyl and $R_2$ and $R_3$ are methyl). Addition of triethylamine (81.3 g, 0.8039 moles) and acetyl chloride (30.0 g, 0.3828 moles) at 20-25° C. for 2-4 hours then addition of water (650 mL) precipitates the crude product. Filtration, washing with water (300 mL) then drying yields (4R,5R)-3-acetyl-2,2-dimethyl-4-hydroxymethyl-5-[4-(methylsulfonyl)phenyl]-1,3-oxazolidine (Compound II).

Example 4

Preparation of (4R,5R)-3-propionyl-2,2-dimethyl-4-hydroxymethyl-5-[4-(methylsulfonyl)phenyl]-1,3-oxazolidine (Compound V: $R_1$ is methylsulfonyl, $R_2$ and $R_3$ are methyl and $R_4$ is ethyl)

(2S,3R)-Methyl-2-amino-3-[4-(methylsulfonyl)phenyl]-3-hydroxy-propanoate (Compound VI: $R_1$ is methylsulfonyl and $R_5$ is methyl) (75 g, 0.2744 moles) in 350 mL of methanol reacts with sodium borohydride (16.6 g, 0.4390 moles) over 4-8 hours at 50-60° C. to quantitatively yield (1R,2R)-2-amino-1-[4-methylsulfonyl)phenyl]-1,3-propandiol (Compound VII: $R_1$ is methylsulfonyl) (67.31 g, 0.2744 moles) in solution. Addition of 20% hydrochloric acid and 2,2-dimethoxypropane (35.7 g, 0.3430 moles) with agitation at 25-35° C. for 3-5 hours then addition of xylene (650 mL) and heating to 75-85° C. for a further 12-16 hours yields (4R,5R)-2,2-dimethyl-4-hydroxymethyl-5-[4-(methylsulfonyl)phenyl]-1,3-oxazolidine (Compound VII: $R_1$ is methylsulfonyl and $R_2$ and $R_3$ are methyl). Addition of triethylamine (52.1 g, 0.5145 moles) and propionyl chloride (31.7 g, 0.3430 moles) at 20-25° C. for 2-4 hours then addition of water (625 mL) precipitates the crude product. Filtration, washing with water (300 mL) then drying yields (4R,5R)-3-propionyl-2,2-dimethyl-4-hydroxymethyl-5-[4-(methylsulfonyl)phenyl]-1,3-oxazolidine (Compound V: $R_1$ is methylsulfonyl, $R_2$ and $R_3$ are methyl and $R_4$ is ethyl).

Example 5

Preparation of (4S,5R)-3-acetyl-2,2-dimethyl-4-fluoromethyl-5-[4-(methylsulfonyl)phenyl]-1,3-oxazolidine (Compound IX: $R_1$ is methylsulfonyl; $R_2$, $R_3$ and $R_4$ are methyl)

(4R,5R)-3-acetyl-2,2-dimethyl-4-hydroxymethyl-5-[4-(methylsulfonyl)phenyl]-1,3-oxazolidine (Compound II) (75 g, 0.2291 moles) in methylene chloride (525 ml) reacts with N,N-diethyl-1,1,2,3,3,3-hexafluoro-1-propanamine (Ishikawa Reagent) (76.7 g, 0.3437 moles) at 95-105° C. for about 4 hours. Cooling to 20-25° C., addition to sodium hydroxide (6 g) in water (2500 mL), separation of the methylene chloride layer, distillation and replacement of methylene chloride by isopropanol (750 mL), precipitates the desired product. Filtration, washing with water (100 mL) and isopropanol (75 mL), then drying yields (4S,5R)-3-acetyl-2,2-dimethyl-4-fluoromethyl-5-[4-(methylsulfonyl)phenyl]-1,3-oxazolidine (Compound IX: $R_1$ is methylsulfonyl; $R_2$, $R_3$ and $R_4$ are methyl).

Example 6

Preparation of (4S,5R)-3-propionyl-2,2-dimethyl-4-fluoromethyl-5-[4-(methylsulfonyl)phenyl]-1,3-oxazolidine (Compound IX: $R_1$ is methylsulfonyl, $R_2$ and $R_3$ are methyl and $R_4$ is ethyl)

(4R,5R)-3-propionyl-2,2-dimethyl-4-hydroxymethyl-5-[4-(methylsulfonyl)phenyl]-1,3-oxazolidine (Compound V: $R_1$ is methylsulfonyl, $R_2$ and $R_3$ are methyl and $R_4$ is ethyl) (70 g, 0.2050 moles) in methylene chloride (450 ml) reacts with N,N-diethyl-1,1,2,3,3,3-hexafluoro-1-propanamine (Ishikawa Reagent) (73.2 g, 0.328 moles) at 95-105° C. for 2-4 hours. Cooling to 20-25° C., quenching with 25% aqueous sodium hydroxide and water (2000 mL) and separation of the methylene chloride layer gives a solution of (4S,5R)-3-propionyl-2,2-dimethyl-4-fluoromethyl-5-[4-(methylsulfonyl)phenyl]-1,3-oxazolidine (Compound IX: $R_1$ is methylsulfonyl, $R_2$ and $R_3$ are methyl and $R_4$ is ethyl) for use in the next step.

Example 7

Preparation of (1R,2S)-2-dichloroacetamido-3-fluoro-1-[4-(methylsulfonyl)phenyl]-1-propanol (Florfenicol)

(4S,5R)-3-acetyl-2,2-dimethyl-4-fluoromethyl-5-[4-(methylsulfonyl)phenyl]-1,3-oxazolidine (Compound IX: $R_1$ is methylsulfonyl; $R_2$, $R_3$ and $R_4$ are methyl) (50.0 g, 0.1518 moles) hydrolyses in water (300 mL) containing 20% hydrochloric acid at 90 to 100° C. over about 1 hour. Adjusting the pH to greater than 12 by addition of sodium hydroxide and extraction with methylene chloride (500 mL) yields (1R,2S)-1-[4-(methylsulfonylphenyl]-2-amino-3-fluoro-1-propanol (Compound Xa) in solution. Methanol (100 mL) replaces methylene chloride which distills off. Addition of methyl dichloroacetate (65.1 g, 0.4554 moles) and triethylamine (16.1 g, 0.1594 moles) with agitation for 12-16 hours at 20-25° C. then addition of water (175 mL) and toluene (100 mL) precipitates the product. Filtration, washing with water (100 mL) and toluene (175 mL) then drying yields (1R,2S)-2-dichloroacetamido-3-fluoro-1-[4-(methylsulfonyl)phenyl]-1-propanol (Florfenicol).

Example 8

Preparation of (1R,2S)-2-dichloroacetamido-3-fluoro-1-[4-(methylsulfonyl)phenyl]-1-propanol (Florfenicol)

(4S,5R)-3-acetyl-2,2-dimethyl-4-fluoromethyl-5-[4-(methylsulfonyl)phenyl]-1,3-oxazolidine (Compound IX: $R_1$ is methylsulfonyl; $R_2$, $R_3$ and $R_4$ are methyl) (50.0 g, 0.1518 moles) hydrolyses in water (300 mL) containing 20% hydrochloric acid at 90 to 100° C. over about 1 hour. Adjusting the pH to greater than 12 by addition of sodium hydroxide and extraction with methylene chloride (500 mL) yields (1R,2S)-1-[4-(methylsulfonyl)phenyl]-2-amino-3-fluoro-1-propanol (Compound Xa) in solution. Addition of triethylamine (16.9 g, 0.1670 moles) and dichloroacetyl chloride (24.6 g, 0.1670 moles) at 20-30° C. for 4-6 hours then removal of methylene chloride by distillation and replacement by toluene (350 mL) and water (100 mL) precipitates the product. Filtration, washing with water (150 mL) and toluene (150 mL) then drying yields (1R,2S)-2-dichloroacetamido-3-fluoro-1-[4-(methylsulfonyl)phenyl]-1-propanol (Florfenicol).

Example 9

Purification of (1R,2S)-2-dichloroacetamido-3-fluoro-1-[4-(methylsulfonyl)phenyl]-1-propanol (Florfenicol)

(1R,2S)-2-dichloroacetamido-3-fluoro-1-[4-(methylsulfonyl)phenyl]-1-propanol (Florfenicol) (45 g, 0.1256 moles) dissolves in water (115 mL) and isopropanol (115 mL) at reflux. Cooling to 20-25° C., filtration of the solids, washing with 1 to 1 water/isopropanol (50 mL) then drying gives pure (1R,2S)-2-dichloroacetamido-3-fluoro-1-[4-(methylsulfonyl)phenyl]-1-propanol (Florfenicol).

Example 10

Preparation and Purification of (1R,2S)-2-dichloroacetamido-3-fluoro-1-[4-(methylsulfonyl)phenyl]-1-propanol (Florfenicol)

(4S,5R)-3-acetyl-2,2-dimethyl-4-fluoromethyl-5-[4-(methylsulfonyl)phenyl]-1,3-oxazolidine (Compound IX: $R_1$ is methylsulfonyl; $R_2$, $R_3$ and $R_4$ are methyl) (50.0 g, 0.1518 moles) hydrolyses in water (300 mL) containing 20% hydrochloric acid at 90 to 100° C. over about 1 hour. Washing with methylene chloride (200 mL), adjusting the pH to greater than 12 by addition of sodium hydroxide and extraction with methylene chloride (300 mL) yields (1R,2S)-1-[4-(methylsulfonyl)phenyl]-2-amino-3-fluoro-1-propanol (Compound Xa) in solution. Methanol (100 mL) replaces methylene chloride which distills off. Addition of methyl dichloroacetate (65.1 g, 0.4554 moles) and triethylamine (16.1 g, 0.1594 moles) with agitation for 12-16 hours at 20-25° C. then addition of water (175 mL) and toluene (100 mL) precipitates the crude product. Filtration, washing with water (100 mL) and toluene (174 mL) then dissolution in water (115 mL) and isopropanol (115 mL) at reflux, cooling to 20-25° C., filtration of the solids, washing with 1 to 1 water/isopropanol (50 mL) then drying gives pure (1R,2S)-2-dichloroacetamido-3-fluoro-1-[4-(methylsulfonyl)phenyl]-1-propanol (Florfenicol).

Example 11

Preparation and Purification of (1R,2S)-2-dichloroacetamido-3-fluoro-1-[4-(methylsulfonyl)phenyl]-1-propanol (Florfenicol)

Methylene chloride (450 mL) distills from a solution of (4S,5R)-3-propionyl-2,2-dimethyl-4-fluoromethyl-5-[4-

(methylsulfonyl)phenyl]-1,3-oxazolidine (Compound IX: $R_1$ is methylsulfonyl, $R_2$ and $R_3$ are methyl and $R_4$ is ethyl) (50.0 g, 0.1456 moles) after addition of water (300 mL) containing 20% hydrochloric acid and heating to 90-100° C. for 2-4 hours. Adjusting the pH to greater than 12 by addition of sodium hydroxide and extraction with methylene chloride (350 mL) yields a solution of (1R,2S)-1-[4-(methylsulfonyl)phenyl]-2-amino-3-fluoro-1-propanol (Compound Xa). Methanol (150 mL) replaces methylene chloride which distills off. Addition of methyl dichloroacetate (52.0 g, 0.3640 moles) and triethylamine (11.0 g, 0.1092 moles) with agitation for 12-16 hours at 20-25° C. then addition of water (150 mL) and toluene (100 mL) precipitates the crude product. Filtration, washing with water (75 mL) and toluene (125 mL) then dissolution in water (50 mL) and isopropanol (100 mL) at reflux, cooling to 20-25° C., filtration of the solids, washing with 1 to 1 water/isopropanol (50 mL) then drying gives pure (1R,2S)-2-dichloroacetamido-3-fluoro-1-[4-(methylsulfonyl)phenyl]-1-propanol (Florfenicol).

Example 12

Preparation of (4R,5R)-3-dichloroacetyl-2,2-dimethyl-4-hydroxymethyl-5-[4-(methylsulfonyl)phenyl]-1,3-oxazolidine (Compound XIIa)

(2S,3R)-Ethyl-2-amino-3-[4-(methylsulfonyl)phenyl]-3-hydroxy-propanoate (Compound IV) (100 g, 0.3480 moles) in 500 mL of methanol reacts with 2,2-dimethoxypropane (39.9 g, 0.3828 moles) and lithium carbonate at 60-70° C. to yield (4S,5R)-2,2-dimethyl-4-ethylcarboxyl-5-[4-(methylsulfonyl)phenyl]-1,3-oxazolidine (Compound XIVa) (113.9 g, 0.3480 moles). Addition of potassium borohydride (28.2 g, 0.5220 moles) with stirring over 4-8 hours at 50-60° C. then yields (4R,5R)-2,2-dimethyl-4-hydroxymethyl-5-[4-(methylsulfonyl)phenyl]-1,3-oxazolidine (Compound VIIIa). Addition of potassium carbonate (19.0 g, 0.1914 moles) and dichloroacetyl chloride (56.4 g, 0.3828 moles) at 20-25° C. for 2-4 hours then addition of water (500 mL) precipitates the crude product. Filtration, washing with water (250 mL) then drying yields (4R,5R)-3-dichloroacetyl-2,2-dimethyl-4-hydroxymethyl-5-[4-(methylsulfonyl)phenyl]-1,3-oxazolidine (Compound XIIa).

Example 13

Preparation of (4S,5R)-3-dichloroacetyl-2,2-dimethyl-4-fluoromethyl-5-[4-(methylsulfonyl)phenyl]-1,3-oxazolidine (Compound XIIIa)

(4R,5R)-3-dichloroacetyl-2,2-dimethyl-4-hydroxymethyl-5-[4-(methylsulfonyl)phenyl]-1,3-oxazolidine (Compound XIIa) (81 g, 0.2050 moles) in methylene chloride (450 ml) reacts with N,N-diethyl-1,1,2,3,3,3-hexafluoro-1-propanamine (Ishikawa Reagent) (73.2 g, 0.328 moles) at 95-105° C. for 2-4 hours. Cooling to 20-25° C., quenching with 25% aqueous sodium hydroxide and water (2000 mL) and separation of the methylene chloride layer gives a solution of (4S,5R)-3-dichloroacetyl-2,2-dimethyl-4-fluoromethyl-5-[4-(methylsulfonyl)phenyl]-1,3-oxazolidine (Compound XIIIa) for use as an intermediate for the next step in the process.

Example 14

Preparation of (1R,2S)-2-dichloroacetamido-3-fluoro-1-[4-(methylsulfonyl)phenyl]-1-propanol (Florfenicol)

(4S,5R)-3-dichloroacetyl-2,2-dimethyl-4-fluoromethyl-5-[4-(methylsulfonyl)phenyl]-1,3-oxazolidine (Compound XIIIa) (60.5 g, 0.1519 moles) selectively hydrolyses in methylene chloride (300 mL) and water (100 mL) containing p-toluene sulfonic acid at 60° C. over several hours. Removal of the methylene chloride by distillation and cooling to 20-25° C. precipitates the product. Filtration, washing with water (100 mL) and toluene (100 mL) then drying yields (1R,2S)-2-dichloroacetamido-3-fluoro-1-[4-(methylsulfonyl)phenyl]-1-propanol (Florfenicol).

What is claimed is:

1. A process for preparing a compound of Formula XI:

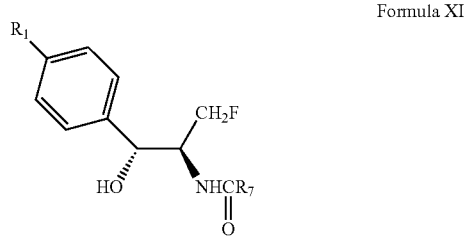

Formula XI wherein:

$R_1$ is hydrogen, methylthio, methylsulfoxy, methylsulfonyl, fluoromethylthio, fluoromethylsulfoxy, fluoromethylsulfonyl, nitro, fluoro, bromo, chloro, acetyl, benzyl, phenyl, halo substituted phenyl, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{2-6}$ heterocyclic group; and $R_7$ is hydrogen, $C_{1-6}$ alkyl, $C_{1-6}$ haloalkyl, $C_{1-6}$ dihaloalkyl, $C_1$ trihaloalkyl, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{2-6}$ heterocyclic benzyl, phenyl or phenyl alkyl where the phenyl ring may be substituted by one or two halogens, $C_{1-6}$ alkyl or $C_{1-6}$ alkoxy comprising:

a) reacting a compound of Formula VI:

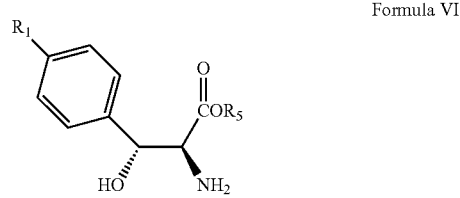

Formula VI wherein:

$R_1$ is as defined above;

$R_5$ is hydrogen, $C_{1-6}$ alkyl, $C_{3-8}$ cycloalkyl, benzyl, phenyl or $C_{1-6}$ phenylalkyl with an oxazolidine forming reagent to form a compound of Formula XIV:

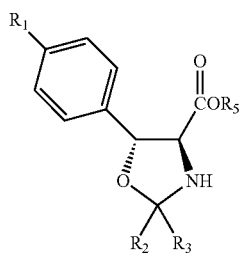

Formula XIV wherein:

$R_1$ and $R_5$ are as defined above;

$R_2$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl, or $C_{2-6}$ heterocyclic group;

$R_3$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, aryl or $C_{2-6}$ heterocyclic group;

b) reducing in situ the compound of Formula XIV with a reducing agent in an alcoholic solvent to form a compound of Formula VIII:

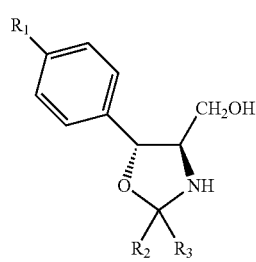

Formula VIII wherein:

$R_1$, $R_2$ and $R_3$ are as defined above;

c) reacting the compound of Formula VIII in situ with a third N-acylating agent to form an oxazolidine protected aminodiol compound of Formula XII:

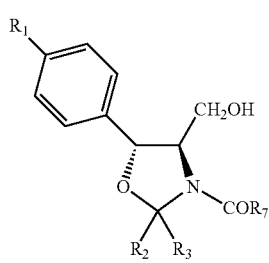

Formula XII wherein:

$R_1$, $R_2$, $R_3$ and $R_7$ are as defined above;

d) fluorinating the compound of Formula V with a fluorinating agent in the presence of an organic solvent to obtain a compound of Formula XIII:

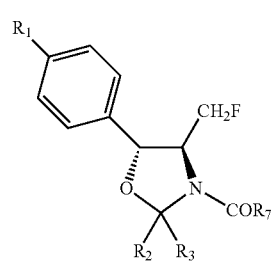

Formula XIII wherein:

$R_1$, $R_2$, $R_3$ and $R_7$ are as defined above; and e) selectively hydrolyzing the compound of Formula XIII with an acid or base catalyst to form a compound of Formula XI.

2. The process of claim 1, wherein $R_1$ is methylthio, methylsulfoxy, or methylsulfonyl.

3. The process of claim 2, wherein $R_1$ is methylsulfonyl.

4. The process of claim 1, wherein $R_2$ and $R_3$ are H, methyl, ethyl or propyl.

5. The process of claim 4, wherein $R_2$ and $R_3$ are methyl.

6. The process of claim 1, wherein $R_5$ is methyl, ethyl, n-propyl, isopropyl, butyl, t-butyl, or pentyl.

7. The process of claim 1, wherein $R_7$ is $CH_2Cl$, $CHCl_2$, $CCl_3$, $CH_2Br$, $CHBr_2$, $CBr_3$, $CH_2F$, $CHF_2$, or $CF_3$.

8. The process of claim 1, wherein the compound of Formula VI is

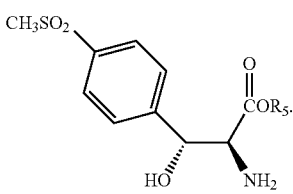

9. The process of claim 8, wherein the compound of Formula VI is

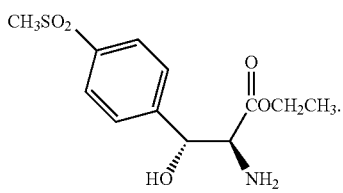

10. The process of claim 8, wherein the compound of Formula VI is

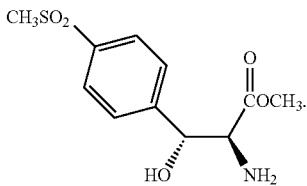

11. The process of claim 1, wherein the oxazolidine forming reagent is selected from the group consisting of formaldehyde, acetone, 2-methoxypropene, 2,2-dimethoxypropane, 2,2-diethoxypropane and mixtures thereof.

12. The process of claim 11, wherein the oxazolidine forming reagent is 2,2-dimethoxypropane.

13. The process of claim 12, wherein the ratio of 2,2-dimethoxypropane to the compound of Formula VI is between about 1:1 and 5:1.

14. The process of claim 13, wherein the ratio of 2,2-dimethoxypropane to the compound of Formula VI is about 1:1.

15. The process of claim 1, wherein the ester oxazolidine forming solvent is the oxazolidine forming reagent itself or an alcoholic solvent.

16. The process of claim 15, wherein the ester oxazolidine forming solvent is methanol, ethanol, propanol, isopropanol, butanol, pentanol and mixtures thereof.

17. The process of claim 16, wherein the ester oxazolidine forming solvent is methanol.

18. The process of claim 1, wherein the ester oxazolidine promoting base is lithium carbonate, lithium carbonate, triethylamine or trimethylamine.

19. The process of claim 18, wherein the ester oxazolidine promoting base is lithium carbonate.

20. The process of claim 1, wherein the ester oxazolidine promoting temperature is less than 80° C.

21. The process of claim 1, wherein the compound of Formula XIV is:

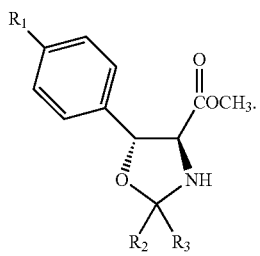

22. The process of claim 1, wherein the compound of Formula XIV is:

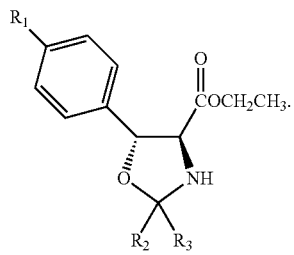

23. The process of claim 21, wherein the compound of Formula XIV is:

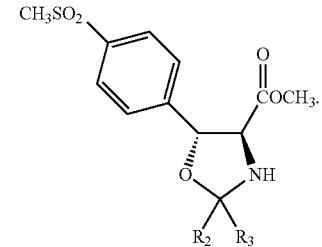

24. The process of claim 22, wherein the compound of Formula XIV is:

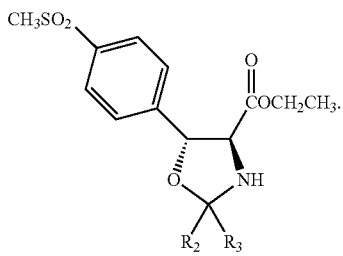

25. The process of claim 23, wherein the compound of Formula XIV is:

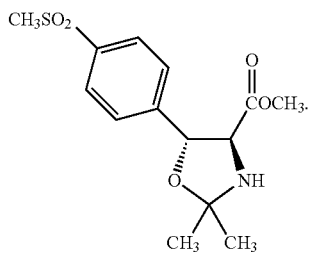

26. The process of claim 24, wherein the compound of Formula XIV is:

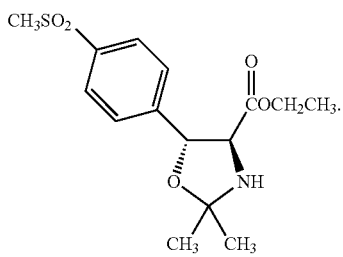

27. The process of claim 1, wherein the reducing agent is selected from the group consisting of $NaBH_4$, $KBH_4$, $Ca(BH_4)_2$, and $LiBH_4$ and mixtures thereof.

28. The process of claim 27, wherein the reducing agent is $KBH_4$.

29. The process of claim 28, wherein the molar ratio of $KBH_4$ to the compound of Formula VI is between about 1:1 and 2:1.

30. The process of claim 29, wherein the molar ratio of $KBH_4$ to the compound of Formula VI is about 1.5:1.

31. The process of claim 27, wherein the reduction is carried out at a temperature below 60° C.

32. The process of claim 31, wherein the reduction is complete within 6 hours.

33. The process of claim 1, wherein the alcoholic solvent is selected from the group consisting of methanol, ethanol, propanol, isopropanol, butanol, pentanol, ethylene glycol, glycerin and mixtures thereof.

34. The process of claim 33, wherein the solvent is methanol or ethanol.

35. The process of claim 34, wherein the solvent is methanol.

36. The process of claim 1, wherein the compound of Formula VIII is

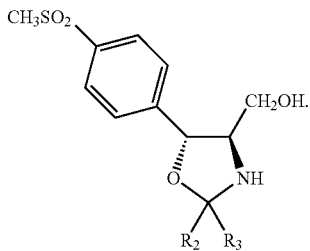

37. The process of claim 36, wherein the compound of Formula VIII is

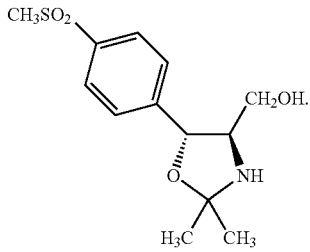

38. The process of claim 1, wherein the third N-acylating agent is of the formula: formula $R_6COR_7$ wherein:

$R_6$ is halo or $C_{1-6}$ alkoxy; and $R_7$ is hydrogen, $C_{1-6}$ alkyl, $C_{1-6}$ haloalkyl, $C_{1-6}$ dihaloalkyl, $C_{1-6}$ trihaloalkyl, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{2-6}$ heterocyclic, benzyl, phenyl or phenyl alkyl where the phenyl ring may be substituted by one or two halogens, $C_{1-6}$ alkyl or $C_{1-6}$ alkoxy.

39. The process of claim 38, wherein $R_6$ is Cl, Br, methoxy or ethoxy.

40. The process of claim 39, wherein $R_6$ is Cl.

41. The process of claim 38, wherein $R_7$ is $CH_2Cl$, $CHCl_2$, $CCl_3$, $CH_2Br$, $CHBr_2$, $CBr_3$, $CH_2F$, $CHF_2$, or $CF_3$.

42. The process of claim 41, wherein $R_7$ is $CHCl_2$.

43. The process of claim 38, wherein the third N-acylating agent is selected from the group consisting of methyldichloroacetate, ethyldichloroacetate, dichloroacetylchloride, methylchloroacetate, ethylchloroacetate, chloroacetylchloride, methyltrichloroacetate, ethyltrichloroacetate, trichloroacetylchloride, methyldifluoroacetate, ethyldifluoroacetate, difluoroacetylchloride, methylfluoroacetate, ethylfluoroacetate, fluoroacetylchloride, methyltrifluoroacetate, ethyltrifluoroacetate, trifluoroacetylchloride, dichloroacetylbromide, difluoroacetylbromide, acetylchloride, acetylbromide and mixtures thereof.

44. The process of claim 43, wherein the third N-acylating agent is methyldichloroacetate or dichloroacetylchloride.

45. The process of claim 44, wherein the third N-acylating agent is dichloroacetylchloride.

46. The process of claim 1, wherein the third N-acylating base is selected from the group consisting of potassium carbonate, sodium carbonate, trimethylamine and triethylamine.

47. The process of claim 46, wherein the third N-acylating base is potassium carbonate or triethylamine.

48. The process of claim 47, wherein the molar equivalent ratio of the third N-acylating base to the compound of Formula VII is between 1:1 and 3:1.

49. The process of claim 48, wherein the molar equivalent ratio of the third N-acylating base to the compound of Formula VIII is about 1.1:1.

50. The process of claim 49, wherein the molar ratio of dichloroacetyl chloride to the compound of Formula VIII is between about 1:1 and 3:1.

51. The process of claim 50, wherein the molar ratio of dichloroacetyl chloride to the compound of Formula VIII is about 1.1 to 1.

52. The process of claim 43, wherein the third N-acylation step is carried out at a temperature between 20-30° C.

53. The process of claim 52, wherein the third N-acylation reaction is complete within 2-4 hours.

54. The process of claim 1, wherein the compound of Formula XII is:

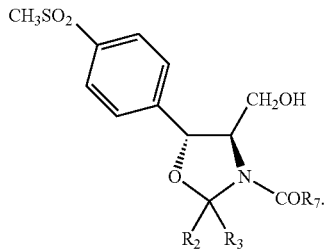

55. The process of claim 54, wherein the compound of Formula XII is:

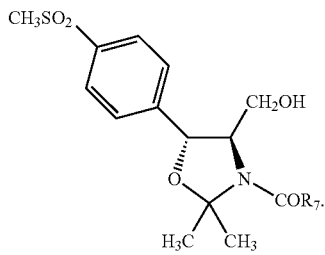

56. The process of claim 54, wherein the compound of Formula XII is:

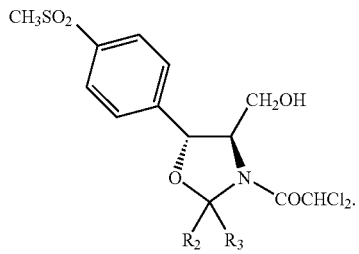

57. The process of claim 56, wherein the compound of Formula XII is:

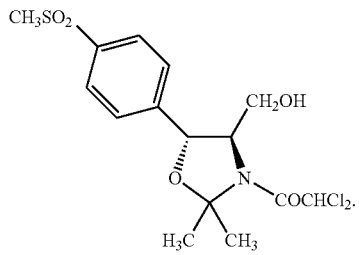

58. The process of claim 1, wherein the fluorinating agent is selected from the group consisting of N-(2-chloro-1,1,2-trifluoroethyl)diethylamine, N-(2-chloro-1,1,2-trifluor-oethyl)dimethylamine, N-(2-chloro-1,1,2-trifluoroethyl)dipropylamine, N-(2-chloro-1,1,2-trifluoroethyl)pyrrolidine, N-(2-chloro-1,1,2-trifluoroethyl)-2-methylpyrrolidine, N-(2-chloro-1,1,2-trifluoroethyl)-4-methylpiperazine, N-(2-chloro-1,1,2-trifluoroethyl)-morpholine, N-(2-chloro-1,1,2-trifluoroethyl)piperidine, 1,1,2,2-tetrafluoroethyl-N,N-dimethylamine, (Diethylamino)sulfurtrifluoride, Bis-(2-methoxyethyl)aminosulfurtrifluoride, N,N-diethyl-1,1,2,3,3,3-hexafluoro-1-propanamine (Ishikawa Reagent) and mixtures thereof.

59. The process of claim 58, wherein the fluorinating agent is N,N-diethyl-1,1,2,3,3,3-hexafluoro-1-propanamine.

60. The process of claim 59, wherein the molar ratio of N,N-diethyl-1,1,2,3,3,3-hexafluoro-1-propanamine to the compound of Formula XII is between about 1:1 and 2:1.

61. The process of claim 60, wherein the molar ratio of N,N-diethyl-1,1,2,3,3,3-hexafluoro-1-propanamine to the compound of Formula XII is about 1.5:1.

62. The process of claim 61, wherein the fluorinating step is carried out at a temperature of from about 80° C. to about 110° C. and at a pressure of about 60 psi.

63. The process of claim 1, wherein the organic solvent is selected from the group consisting of 1,2-dichloroethane, methylene chloride, chloroform, chlorobenzene, chlorinated hydrocarbons and mixtures thereof.

64. The process of claim 63, wherein the organic solvent is methylene chloride.

65. The process of claim 1, wherein the compound of Formula XIII is

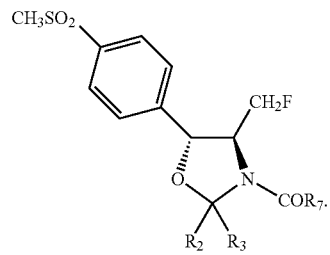

66. The process of claim 65, wherein the compound of Formula XIII is

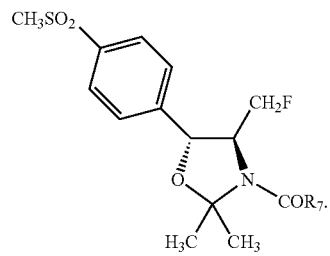

67. The process of claim 65, wherein the compound of Formula XIII is

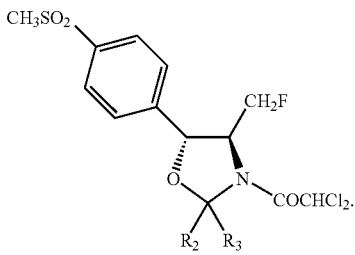

68. The process of claim 67, wherein the compound of Formula XIII is

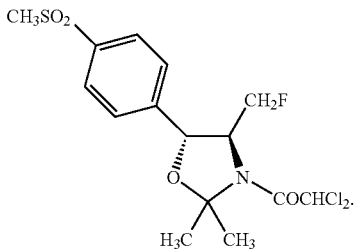

69. The process of claim 1, wherein the compound of Formula XI is

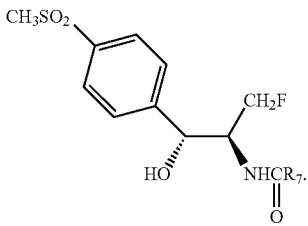

70. The process of claim 69, wherein the compound of Formula XI is Florfenicol

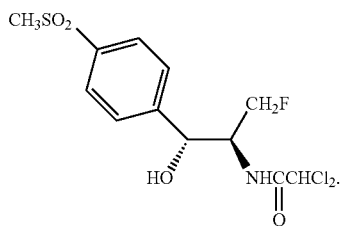

71. The process of claim 1, wherein the acid catalyst is dilute aqueous hydrochloric acid, sulfuric acid, or phosphoric acid, methanesulfonic acid or p-toluene sulfonic acid.

72. The process of claim 71, wherein the acid catalyst is p-toluene sulfonic acid.

73. The process of claim 1, wherein the base catalyst is LiOH, NaOH, KOH, $Li_2CO_3$, $Na_2CO_3$, $K_2CO_3$, sodium methoxide, sodium ethoxide, potassium methoxide and potassium ethoxide.

74. The process of claim 73, wherein the base catalyst is $K_2CO_3$.

75. The process of claim 74, wherein the temperature of the selective hydrolysis is below 80° C.

76. The process of claim 1, wherein methylene chloride is the organic solvent for the selective hydrolysis.

77. The process of claim 1, wherein the compound of Formula XI is purified with a mixture of a $C_{1-10}$ alkyl mono, di or tri alcohol and water to form the pure form of a compound of Formula XI.

78. The process of claim 77, wherein the purification is carried out in a mixture of methanol, ethanol, propanol, isopropanol, butanol, sec-butanol, t-butanol, pentanol, ethylene glycol, propylene glycol, butylene glycol or glycerin and water.

79. The process of claim 78, wherein the purification is carried out in a mixture of methanol, ethanol, propanol, isopropanol, butanol, sec-butanol, t-butanol, or pentanol and water.

80. The process of claim 79, wherein the purification is carried out in a mixture of isopropanol and water.

81. The process of claim 80, wherein the ratio of isopropanol to water is between 1:5 and 5:1.

82. The process of claim 81, wherein the ratio of isopropanol to water is 1:1.

83. The process of claim 82, wherein the dissolution temperature for purification is the reflux point of 1:1 isopropanol and water.

84. The process of claim 77, wherein the purification reaction is cooled to 10-30° C. to crystallize the desired compound.

85. The process of claim 84, wherein the purification reaction is cooled to about 20-25° C. to crystallize the desired compound.

* * * * *